United States Patent [19]

Bonner

[11] Patent Number: 4,519,163

[45] Date of Patent: May 28, 1985

[54] CONTROLLED GROWTH OF MUNG BEAN SPROUTS

[75] Inventor: James F. Bonner, South Pasadena, Calif.

[73] Assignee: Phytogen, Pasadena, Calif.

[21] Appl. No.: 530,854

[22] Filed: Sep. 9, 1983

Related U.S. Application Data

[63] Continuation-in-part of Ser. No. 421,128, Sep. 22, 1982, abandoned.

[51] Int. Cl.$^3$ .............................................. A01B 79/00
[52] U.S. Cl. ................................... 47/58; 47/DIG. 5; 47/DIG. 9; 71/86; 71/117; 71/127
[58] Field of Search ..................... 47/14–16, 47/57.6, 58–64, DIG. 5, DIG. 9, 1, 56; 71/77, 117, 110, 86, 127

[56] References Cited

U.S. PATENT DOCUMENTS

| | | | |
|---|---|---|---|
| 2,522,409 | 9/1950 | Stoller | 71/77 |
| 2,736,643 | 2/1956 | Pentler et al. | 71/77 |
| 3,567,421 | 3/1971 | Pape et al. | 71/77 |
| 3,578,435 | 5/1971 | Ushioda | 47/79 |
| 3,661,549 | 5/1972 | Fretag et al. | 47/58 |
| 4,171,968 | 10/1979 | Farone | 71/77 |
| 4,227,911 | 10/1980 | Leonard et al. | 71/77 |
| 4,374,661 | 2/1983 | Fritz et al. | 71/86 |

FOREIGN PATENT DOCUMENTS 485717  1/1976  U.S.S.R. .................. 47/DIG. 9

Primary Examiner—James R. Feyrer
Attorney, Agent, or Firm—Christie, Parker & Hale

[57] ABSTRACT

Mung bean sprouts of increased diameter are grown in an atmosphere containing oxygen and from about 0.5 to about 3 ppmv of a plant-growth regulator of ethylene, acetylene or mixtures thereof, and under a spray of an aqueous solution containing from about 0.1 to about 5 ppm weight-to-volume of a plant-growth hormone, which is 2,4-D, an auxin, or mixtures thereof.

18 Claims, No Drawings

CONTROLLED GROWTH OF MUNG BEAN SPROUTS

CROSS-REFERENCE TO RELATED APPLICATIONS

This application is a continuation-in-part of my application Ser. No. 421,128, filed Sept. 22, 1982, now abandoned.

BACKGROUND OF THE INVENTION

Mung beans (*Phaseolus arueus*) are germinated in darkness to produce seedlings which are a common article of the Oriental cuisine. They are also used as an attractive adornment to salads in other cuisines.

The general method of producing mung bean sprouts has been to place a layer of seeds on the bottom of a container having drainage facilities. The beans are soaked for 10 or more hours, then sprinkled with water, generally intermittently, in the absence of light. After 5 to 6 days, the mung bean sprouts are harvested for consumption. They can average, for domestic species, from about 2 to about 2.5 mm in diameter, and are about 5 cm in length.

The present invention is directed to a method to enhance the diameter of such sprouts without a material sacrifice in length.

SUMMARY OF THE INVENTION

According to the invention, there is provided a process to materially increase the diameter-to-length ratio of mung bean sprouts, employing a plant-growth hormone in combination with a plant-growth regulator.

In particular, mung bean sprouts of increased diameter and/or reduced root growth or free of roots are grown by a process which comprises, after achieving sprouting, exposing the sprouted mung beans in the absence of light to a spray of aqueous plant-growth hormone solution comprising a plant-growth hormone, an auxin or biological analogues thereof, and present in the aqueous plant-growth hormone solution in a concentration of from about 0.1 to about 5 ppm by weight to volume of said aqueous solution and to a plant-growth regulator atmosphere comprising oxygen and from about 0.5 to about 3 ppm by volume of a plant-growth regulator selected from the group consisting of ethylene, acetylene and mixtures thereof for at least a portion of a first period of mung bean sprout growth. The preferred concentration of plant-growth regulator is from about 0.75 to about 2.5 ppmv, with a concentration of from about 1 to about 2 most preferred. The preferred plant-growth hormone is 2,4-dichlorophenoxy acetic acid, preferably present in a concentration of from about 0.2 to about 3 ppm weight-to-volume.

For a final period of growth, exposure to the aqueous solution of plant-growth hormone is terminated. During this final period of growth, the mung bean sprouts are exposed to a spray of water at least essentially free of plant-growth hormone, preferably deionized water. This may be used to eliminate any plant-growth hormone which may be retained by the mung bean sprouts. The atmosphere may be continued as such, or may be converted to an oxygen-containing atmosphere at least essentially free of the plant-growth regulator. A convenient oxygen-containing atmosphere is air.

It is preferred to conduct the process under aseptic conditions, and to provide in the aqueous solution employed a surfactant which disperses the plant-growth hormone and which aids in removing the hormone from grown sprouts and in germinating mung beans.

The preferred plant-growth regulator atmosphere comprises about 8 percent by volume oxygen, about 8 percent by volume carbon dioxide, and about 1 ppm by volume ethylene, the balance of said atmosphere being inert and mainly nitrogen.

The first period of growth is normally up to about 120 hours, and the final period of growth is up to about 24 hours.

Preferably, the growing mung bean sprouts are intermittently sprayed for intervals of about 5 minutes approximately each thirty minutes.

In the preferred process, the mung beans are submersed in the absence of light in water containing a surfactant for a period of time of up to about 10 hours to imbibe water and initiate sprout growth. The water is drained from the sprouted mung beans. The growing mung bean sprouts are then exposed to the plant-growth regulator atmosphere comprising oxygen, carbon dioxide, and from about 0.75 to 3 ppmv of a plant-growth regulator selected from the group consisting of ethylene, acetylene and mixtures thereof, and while maintaining said atmosphere the sprouts are exposed to an intermittent spray of water for a first period of about 24 hours, then exposed to a spray of an aqueous plant-growth hormone solution comprising deionized water, from about 0.5 to about 5 ppm of a plant-growth hormone selected from the group consisting of an auxin, a biological equivalent thereof, or mixtures thereof, and a surfactant present in a concentration sufficient to disperse said plant-growth hormone for a second period beginning at about the 24th hour of sprout growth and extending to about the 72nd hour of sprout growth.

The plant-growth hormone is then supplanted by deionized water for a final period of growth. The plant-growth regulator atmosphere may also be replaced with an air atmosphere for the final period of growth, or for a longer time.

There are grown, in accordance with the invention, mung bean sprouts having a diameter substantially greater than that which would otherwise be realized, while still maintaining a reasonable length. A one-hundred-percent increase in sprout diameter, as compared to normal sprout diameter, may be realized.

The flesh of the improved mung bean sprout is turgid and succulent, and analytical tests reveal no detectable residues of plant-growth regulator or plant-growth hormone.

DETAILED DESCRIPTION

According to the present invention, there is provided a process for the controlled growth of mung bean sprouts of substantially increased diameter by exposure of sprouted mung beans to an atmosphere comprising oxygen and a plant-growth regulator in combination with an aqueous spray comprising a plant-growth hormone. As used herein, by the term, "plant-growth hormone", there is meant a natural or synthetic auxin, or biological analogue thereof, introduced to an aqueous solution for spray over the sprouts. Exemplary of an auxin is naphthalene acetic acid. Exemplary of a biological analogue is 2,4-dichlorophenoxy acetic acid. It is presently preferred to employ 2,4-dichlorophenoxy acetic acid (2,4-D), which is provided in its most soluble form, namely, as sodium salt, as amine salts, or as an ester. The 2-methyl-amino salt is presently preferred.

Because auxins or their analogues can vary in their effectiveness, the concentration range of use can be from about 0.1 to about 5 ppm by weight to volume of solution.

The actual lower limit of plant-growth hormone concentration is when there is essentially no reduction in root growth to the benefit of an increase in sprout diameter. An excess of concentration has been observed to be the elimination of root growth, but also the inhibition of an increase in sprout length. It is preferred to adjust concentration to achieve the conventional 5 cm sprout length and an increased diameter of from 30 to 100 percent of original.

The optimum concentration for 2,4-dichlorophenoxy acetic acid, the preferred plant-growth hormone, is in the concentration range of from 0.2 to about 3 ppm. Over this range its effect is optimized.

By a "plant-growth regulator" there is meant ethylene or acetylene, which is present in an atmosphere which otherwise promotes normal growth in a concentration of from about 0.5 to about 3 ppmv, preferably from about 0.75 to about 2.5 ppmv, most preferably from about 1 to about 2 ppmv. The particularly preferred atmosphere containing the plant-growth regulator is one containing about 1 ppm ethylene, 8 percent by volume carbon dioxide, 8 percent by volume oxygen, the balance being inerts and primarily nitrogen. A gas of this composition is readily available in the marketplace, and is known as "banana gas". While carbon dioxide is not an essential requirement of the atmosphere, its presence is desired, as it inhibits respiration.

The ethylene or acetylene may be provided from a solid source, such as chloroethylphosphoric acid, which decomposes at a pH below 7, to release ethylene; calcium carbide, which decomposes in water to release acetylene; and the like.

To enhance uniform dispersion of the plant-growth hormone in the aqueous solution brought into contact with the growing sprouts, there is included a surfactant. Anionic, nonionic, cationic, and amphoteric surfactants, as well as mixtures thereof, may be used. Tween 40, a poly-ethylene oxide sorbitan monopalpitate manufactured and sold by ICI United States, Inc., is exemplary of a functional surfactant. Concentration is sufficient to disperse the plant-growth hormone and to prevent localized enlargment of the bean sprouts.

Plant-growth hormones and plant-growth regulators in the concentrations employed act synergistically to substantially increase the normal diameter of bean sprouts, with or without loss of root growth. Average diameters in the range of from about 3 to about 6 mm are achievable, depending on treating conditions and growth cycle, while maintaining an average length of from about 5 to 6 cm. The mung bean sprouts are characterized as exhibiting a flesh which is turgid and succulent. Moreover, as grown in accordance with the present invention, there is no detectable residue of either the plant-growth regulator or the plant-growth hormone in the product.

With the above in mind, the following is a procedure which may be employed to provide mung bean sprouts of enhanced diameter, utilizing the aqueous plant-growth regulator solution and plant-growth hormone atmosphere or their supplements.

There may be employed as apparatus a tank which is normally constructed of stainless steel to enable sterilization and to preclude the introduction of light. A screen is provided above the floor of the tank to support the mung beans and the sprouts grown therefrom, and to permit process liquors to pass through. To initiate sprouting, a layer of seeds is placed on the screen, covered with water, and allowed to water-soak or imbibe. Preferably, a surface-active agent of the type described above is employed to enhance entry of water into the interstices of the beans. Soaking is for up to about 10 hours, after which the water-soak may be supplanted by exposure to a spray of water in the presence of an atmosphere containing the plant-growth regulator, or a spray of water containing the plant-growth regulator. Continuing processing under aseptic conditions is desired, and the absence of light over at least a portion of the time in which the mung bean sprouts grow is essential to achieve the absence of green color. Mung bean sprouts are brought into contact with an aqueous solution of the plant-growth hormone. Contact with the aqueous solution may be continuous or intermittent. Moreover, flow can be a one-time contact flow or a recycle flow. One-time contact flow with intermittent flow is preferred because of the need to control the concentration of the plant-growth hormone which, in the preferred embodiment, is injected into the water-spray stream by a portional injector. It is preferred that spray be intermittent over any one day of use, and that it occur for about a 5-minute period at about 30-minute intervals. At all times there may be provided a sufficient gaseous flow containing the plant-growth regulator to maintain a constant one-atmosphere pressure in the dark, aseptic growth environment. Treatment can occur throughout the period of growth or in select periods, preferably the intermediate (from about the 24th to about the 72nd) hours of sprout growth. In this instance, the final period may be with or without the plant-growth regulator atmosphere.

Independent of the precise time in which the growing sprouts are exposed to a spray containing plant-growth hormone, during the final period of growth, preferably about the last 24 hours, the spray is discontinued and supplanted by a spray of plain water, which for all operations described herein is preferably deionized. A surfactant may be used to aid in this rinse. The gaseous atmosphere containing the plant-growth regulator may be the same or supplanted by an air atmosphere. Upon completion of the growth cycle, the product will be devoid of any residue of plant-growth hormone. The sprouts are now of an increased diameter of up to one hundred percent greater than that realized in the absence of processing in accordance with this invention.

Water-spray, in addition to providing the plant-growth hormone, also serves to control temperature in the controlled growth chamber by removing the growth exotherm.

EXAMPLE AND CONTROL

Mung beans were submersed in the absence of light in water, in separate containers, for a period of up to about 10 hours to imbibe water and initiate sprout growth. The water was drained from the sprouted mung beans.

For enhanced growth, the watering solution for growing sprouts in one container contained 2,4-D in a concentration of about 3 ppm weight-to-volume. Plain water was used for the control sprouts grown in the other container. For enhanced growth for the container, the air atmosphere on the last day of the 6-day cycle was enriched with ethylene in a concentration of 2 ppmv introduced as Ethrel to the solution of 2,4-D. In all instances, the period of growth was 6 days, with intermittent watering under drainage conditions at a temperature of about 24° C.

The result for 10 plants grown under growth-promoter conditions was a decrease of 38 percent in stem height but a 68-percent increase in width. Plants grown under growth-promoter conditions were substantially root-free and had a fresh weight which was 10 percent greater than that of the controls, with root weight included. Stem volume increased by 80 percent. The raw data for mesocotyl is as follows, in mm:

| Plant | 2,4-D | | | Control | | |
|---|---|---|---|---|---|---|
| | Stem Height | Root Height | Width | Stem Height | Root Height | Width |
| 1 | 60 | 0 | 2.5 | 85 | 60 | 2 |
| 2 | 55 | 0 | 3 | 85 | 30 | 2 |
| 3 | 60 | 0 | 4 | 110 | 50 | 2 |
| 4 | 60 | 0 | 4 | 115 | 50 | 2 |
| 5 | 60 | 0 | 3 | 115 | 35 | 2 |
| 6 | 60 | 0 | 4 | 80 | 40 | 2 |
| 7 | 60 | 0 | 3 | 90 | 40 | 2 |
| 8 | 65 | 0 | 3 | 100 | 60 | 2 |
| 9 | 55 | 0 | 4 | 110 | 40 | 2 |
| 10 | 54 | 0 | 3 | 80 | 50 | 2 |
| Average: | 60 | 0 | 3.35 | 96 | 48 | 2 |
| Total Weight (all 10): | 5.0 gms | | | 4.5 gms | | |

What is claimed is:

1. A process for growing of mung bean sprouts of increased diameter which comprises exposing sprouted mung beans in the absence of light to a spray of aqueous plant-growth hormone solution comprising a plant-growth hormone selected from the group consisting of an auxin, a biological analogue thereof, and mixtures thereof, and present in a concentration of from about 0.1 to about 5 ppm by weight to volume of said aqueous solution and to a plant-growth regulator atmosphere comprising oxygen and from about 0.5 to about 3 ppm by volume of a plant-growth regulator selected from the group consisting of ethylene, acetylene and mixtures thereof for at least a portion of a selected period of mung bean sprout growth.

2. A process as claimed in claim 1 which includes the steps of:
   (a) terminating for a final period of growth, exposure to said aqueous solution of plant-growth hormone; and
   (b) exposing during said final period of growth, said mung bean sprouts to a spray of water at least essentially free of plant-growth hormone.

3. A process as claimed in claim 1 in which the aqueous plant-growth hormone contains a surfactant present in a quantity sufficient to disperse said plant-growth hormone substantially uniformly in said aqueous solution.

4. A process as claimed in claim 3 in which the plant-growth hormone is 2,4-dichlorophenoxy acetic acid.

5. A process as claimed in claim 4 in which the plant-growth regulator atmosphere comprises about 8 percent by volume oxygen, about 8 percent by volume carbon dioxide, and about 1 ppm by volume ethylene, the balance of said atmosphere being inert.

6. A process as claimed in claim 5 in which the selected period of mung bean sprout growth is up to about 144 hours and in which the final period of growth is up to about 24 hours.

7. A process as claimed in claim 6 in which the plant-growth regulator atmosphere is supplanted for the final period of growth by an oxygen-containing atmosphere at least essentially free of plant-growth regulator.

8. A process as claimed in claim 7 in which the oxygen-containing atmosphere is air.

9. A process as claimed in claim 1 in which each spray is for about a 5-minute period at about 30-minute intervals.

10. A process as claimed in claim 4 in which each spray is for about a 5-minute period at about 30-minute intervals.

11. A process for growing mung bean sprouts of increased diameter which comprises:
   (a) exposing during a first period of mung bean sprout growth, in the absence of light and under aseptic conditions, germinated mung beans to an intermittent spray of a deionized aqueous plant-growth solution comprising from about 0.1 to about 5 ppm weight-to-volume of 2,4-dichlorophenoxy acetic acid and a surfactant present in a concentration sufficient to disperse the 2,4-dichlorophenoxy acetic acid in said aqueous plant-growth hormone solution and a plant-growth regulator atmosphere comprising oxygen, carbon dioxide and from about 0.5 to about 5 ppm by volume ethylene, said first period of mung bean sprout growth being up to about 120 hours;
   (b) supplanting said spray of aqueous plant-growth hormone solution with a spray of deionized water and exposing growing mung bean sprouts, in the absence of light, to said intermittent spray of water and air for a period of up to about 24 hours; and
   (c) harvesting the mung bean sprouts.

12. A process as claimed in claim 11 in which each spray is for about a 5-minute period at about 30-minute intervals.

13. A process for growing bean sprouts of increased diameter which comprises:
   (a) submersing, in the absence of light and under aseptic conditions, mung beans in deionized water containing a surfactant for a period of time of up to about 10 hours to initiate growth of sprouts;
   (b) draining the water from the sprouted mung beans;
   (c) introducing to said mung bean sprouts a plant-growth regulator atmosphere comprising oxygen, carbon dioxide and from about 0.5 to about 3 ppm by volume of a plant-growth regulator selected from the group consisting of ethylene, acetylene and mixtures thereof and while maintaining said atmosphere,:
      (i) intermittently exposing said sprouts to deionized water for a first period of at least about 24 hours;
      (ii) intermittently exposing said sprouts to a spray of an aqueous plant-growth hormone solution comprising deionized water, from about 0.1 to about 5 ppm of a plant-growth hormone selected from the group consisting of an auxin, a biological analogue thereof, and mixtures thereof, and a surfactant present in a concentration sufficient to disperse said plant-growth hormone in said aqueous solution for a second period beginning at about the 24th hour of sprout growth and extending to about the 72nd hour of sprout growth; and
   (d) replacing the spray of plant-growth hormone with an intermittent spray of deionized water for a final period of growth of at least about 24 hours.

14. A process as claimed in claim 13 in which the sprouts are intermittently sprayed with deionized water for about 48 hours.

15. A process as claimed in claim 14 in which the plant-growth regulator atmosphere comprises about 8 percent by volume oxygen, about 8 percent by volume carbon dioxide, about 1 ppm by volume ethylene, the balance being inert.

16. A process as claimed in claim 15 in which the plant-growth regulator atmosphere is replaced by air for at least the final period of growth.

17. A process as claimed in claim 13 in which the auqeous plant-growth hormone solution contains from about 0.2 to about 3 ppm by weight 2,4-dichlorophenoxy acetic acid to volume of solution 18. A process as claimed in claim 13 in which each intermittent spray is for about a 5-minute period at about 30-minute intervals.

* * * * *